(12) United States Patent
Goerne et al.

(10) Patent No.: US 9,381,165 B2
(45) Date of Patent: Jul. 5, 2016

(54) MATRIX FOR THE INFILTRATION WITH CELLS

(71) Applicant: Bioenergy Capital AG, Cologne (DE)

(72) Inventors: Martin Goerne, Hamburg (DE); Thomas Kordick, Goldbach (DE)

(73) Assignee: BIOENERGY CAPITAL AG, Cologne (DE)

( * ) Notice: Subject to any disclaimer, the term of this patent is extended or adjusted under 35 U.S.C. 154(b) by 0 days.

(21) Appl. No.: 14/376,131

(22) PCT Filed: Feb. 1, 2013

(86) PCT No.: PCT/EP2013/000324
§ 371 (c)(1),
(2) Date: Jul. 31, 2014

(87) PCT Pub. No.: WO2013/113514
PCT Pub. Date: Aug. 8, 2013

(65) Prior Publication Data
US 2015/0010611 A1    Jan. 8, 2015

(30) Foreign Application Priority Data
Feb. 1, 2012    (EP) .................................... 12000650

(51) Int. Cl.
| | |
|---|---|
| *A61L 27/26* | (2006.01) |
| *A61K 9/70* | (2006.01) |
| *A61L 27/56* | (2006.01) |
| *A61L 27/58* | (2006.01) |
| *A61L 27/34* | (2006.01) |

(Continued)

(52) U.S. Cl.
CPC ............... *A61K 9/7007* (2013.01); *A61K 35/12* (2013.01); *A61L 27/34* (2013.01); *A61L 27/38* (2013.01); *A61L 27/56* (2013.01); *A61L 27/58* (2013.01)

(58) Field of Classification Search
IPC ....................................................... A61L 27/26
See application file for complete search history.

(56) References Cited

U.S. PATENT DOCUMENTS

| | | | |
|---|---|---|---|
| 7,763,456 | B2 | 7/2010 | Li et al. |
| 8,309,115 | B2 | 11/2012 | Goerne et al. |
| 8,828,546 | B2 | 9/2014 | Dias et al. |

(Continued)

FOREIGN PATENT DOCUMENTS

| | | |
|---|---|---|
| EP | 1264607 A1 | 12/2002 |
| EP | 1674048 A1 | 6/2006 |

(Continued)

OTHER PUBLICATIONS

Japanese Office Action issued Jan. 20, 2015 in corresponding Japanese Application No. 2014-555126 (with English translation).

*Primary Examiner* — Rosanne Kosson
(74) *Attorney, Agent, or Firm* — Morris & Kamlay LLP

(57) ABSTRACT

A cell implant matrix has a connective porosity of more than 80% and consists mainly of a mixture of bioresorbable polymers, wherein the matrix has disk-shape and wherein a surface layer on one side of the disk has less than 20% of the average pore density of the other sides.

The matrix is manufactured by providing a bioresorbable polymer layer; stratifying, onto the polymer layer, a mixture of a water-soluble solid, at least two polymers differing with respect to their resorption rates, and a solvent for one of the polymers; evaporating the solvent optionally followed by compacting the mixture; and watering the compacted body to remove the salt.

6 Claims, 1 Drawing Sheet

(51) Int. Cl.
  *A61L 27/38* (2006.01)
  *A61K 35/12* (2015.01)

(56) References Cited

U.S. PATENT DOCUMENTS

| | | |
|---|---|---|
| 2007/0166343 A1 | 7/2007 | Goerne et al. |
| 2009/0130699 A1 | 5/2009 | Goerne et al. |
| 2010/0028405 A1 | 2/2010 | Goerne et al. |
| 2010/0297675 A1 | 11/2010 | Deng et al. |
| 2011/0059874 A1 | 3/2011 | Rooijmans et al. |

FOREIGN PATENT DOCUMENTS

| | | |
|---|---|---|
| EP | 1185621 B1 | 2/2010 |
| JP | 2003024340 A | 1/2003 |
| JP | 2003503318 A | 1/2003 |
| JP | 2005124463 A | 5/2005 |
| JP | 2007527435 A | 9/2007 |
| JP | 2010505393 A | 2/2010 |
| JP | 2010506828 A | 3/2010 |
| JP | 2011513566 A | 4/2011 |
| WO | WO/00/78928 | 12/2000 |
| WO | 2004108810 A1 | 12/2004 |
| WO | 2006061229 A1 | 6/2006 |
| WO | 2010060066 A1 | 5/2010 |

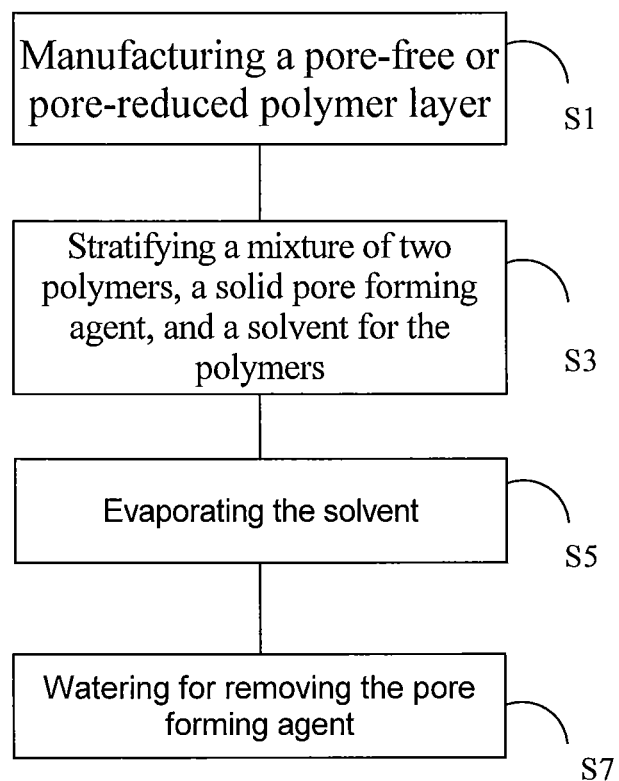

MATRIX FOR THE INFILTRATION WITH CELLS

FIELD OF THE INVENTION

The present application relates to porous matrices for infiltration with cells for therapeutic or diagnostic purposes.

BACKGROUND OF THE INVENTION AND PRIOR ART

Cell implants on the basis of porous matrices made of biocompatible polymers are known from WO 2004/108810 A1. In such matrices, the pores are interconnected and serve as template for the infiltration with cells in vivo (e. g. therapeutic) or in vitro (e. g. diagnostic). For transplantations, such a bioresorbable matrix may serve to temporally localise the transplant.

The known templates are, in some applications, not yet fully satisfying, in particular as regards the clinical performance.

SUMMARY OF THE INVENTION

The invention aims at improving the clinical performance of the templates.

To this end, the invention proposes to provide, on one side of the usually disk-shaped template, a surface with less than 20% of the average pore amount of the other side(s). This asymmetric structure enables positioning the template in the body in such a manner that the implanted viable cells are retained therein longer.

According to a further aspect, the invention proposes a method of manufacturing porous bioresorbable matrices, wherein initially a polymer layer is formed without pore forming agent, onto which a mixture of at least two polymers, a solvent for one of the polymers and a water soluble pore forming agent placed, followed by evaporating the solvent and then watering to remove the pore forming agent. Between these latter two steps, in a variant the application of pressure may occur. Both methods result in highly porous polymeric matrix disks, one side of which is, however, a pore free or at least pore-reduced membrane. Despite this membrane, the supply of the cells present, in use, in the pores is sufficient, but the loss rates due to emigration are considerably reduced. In a variant in which such a template shall serve to support connective tissue, the continuous polymer layer can provide sufficient strength for e.g. suturing material for fixing the template.

In embodiments, the porous matrix is hydrophilically coated, e.g. with polymeric (meth)acrylic acid. TO this end, a plasma coating step is followed by a plasma-less coating step, whereby the required layer thicknesses of above one micrometer are achieved.

DETAILED DESCRIPTION OF THE INVENTION

Further features of the invention are available in the following description of embodiments in conjunction with the claims and the drawings. The invention is not defined by the described embodiments, but by the scope of the accompanying patent claims. In particular, individual features of embodiments of the invention can be realized in a different number and combination than in the examples following hereunder. In the subsequent explanation of an embodiment, reference is made to the accompanying drawing, which shows a flow diagram for a method according to the invention.

In a main application, matrices for implantation with functional cells are provided, for example with hepatocytes and/or with islet-of-Langerhans cells. Such biochemically functional cells adhere to the inner walls of the pores of the foam-like matrix (adhesion rates over 80% or, when suitably coated, over 95%) and may be transplanted with the matrix into mesothelial pockets, ideally of the cell donor itself. Herein it is exploited that in this case, no rejection reaction occurs, but only a comparatively mild foreign body stimulation, which is even beneficial for the therapeutic process. Within a few weeks, the matrix is vascularised and the implanted cells are no more dependent only on diffusive supply. The matrices are arranged so that the pore-reduced (or -free) side is inwards and the pore-rich side is outwards, to maintain the loss rate due to emigration to a low level. In parallel, a gradual resorption of a part of the resorbable matrix takes place (within 3-4 months, or at least 2 and/or less than 7 months) and the physiologic environment is thereby influenced in a manner likewise beneficial for the therapeutic success. It is desirable that a part of the polymer mixture erodes more slowly (ratio of the degradation times at least 5) and maintains the structural integrity for a longer time, e. g. 2.5-3 years (or at least 2 and/or less than 5 years). Such polymers are desirably based on $\alpha$-hydroxycarbonic acids such as lactic acid and/or glycolic acid, e. g. PLA or PLGA. The manufacturers of such polymers certified for use in the human body indicate the nominal degradation times relevant here.

As mentioned above, particularly good adhesion rates are observed with coated matrices, namely ones which are initially plasma coated, in a combined PECVD/CVD-process, with a thin PAA-layer (e.g. 20-30 nm) and are subsequently coated with a thicker PAA-layer (e.g. 20-30 µm) without the action of a plasma. This upper layer forms a crystalline, hydrophilic layer.

Initially, a solution of one of the employed polymers in chloroform certified for medicinal purposes is poured into a mold and the solvent evaporated at 45°-65° C. Next, a polymer mixture having a pre-defined particle size distribution is mixed with a rock salt granulate likewise having a pre-defined particle size distribution, is admixed with a solution of one of the polymers in chloroform and then brought onto the polymer layer already present. From this pre-form, the solvent evaporates at slightly elevated temperature (45° C.-65° C.) and same can be compacted by the application of pressure if desired. subsequently, the pre-form is watered to remove the salt and thereby provide the desired porosity. Herein, the initially manufactured polymer layer remains, however, pore free. According to the field of use, the thickness of the pore-reduced layer can be controlled by the amount and concentration of the initial solution. For example, a very thin membrane is obtained if the concentration of the solution is low (e.g. 4% in chloroform, slowly degradable polymer) and the filling level small (e.g. 0.1-1 mm, for example 0.3 mm). Where a mechanically more enduring structure is desired, the filling level can be set higher (e.g. 5-50 mm, typically 20-25 mm) at the same concentration. The evaporating of the chloroform in this case takes accordingly longer (1.5 h). In the former case the resulting membrane has a thickness of ca. 10-20 µm, in the latter case a thickness of ca. 0.5-1 mm.

The rock salt particles of the stratifying mixture are somewhat more coarse (median at 350-370 µm) than the polymer particles (median of the more slowly degradable polymer between 210 µm and 230 µm, that of the more rapidly degradable polymer between 150 µm and 170 µm). Therein the distribution widths (5%/95%) are similar, namely around ±85-95 µm for salt or total polymer, respectively. The shape of the distribution can be bi- or tri-modal. The composition of the stratifying mixture is about 96% salt, 1-1.5% solid polymer and a further ca. 3-5% dissolved polymer, wherein the volume proportions of solids and liquids are about equal. In total, the proportion of the rapidly degradable polymer is only about 5-20% of the polymers. The total thickness of the pore forming layer is 5-6 mm. In the variant of a more stable initial layer, the salt can be selected somewhat more coarse (median ca. 400-420 µm). In this case the total thickness of the pore forming layer is 4-5 mm and the compacting under pressure can be dispensed with. The watering takes about 24 h and is followed by drying at 45-50° C. When a coating is made, the matrix is placed on the pore reduced side and thus mainly the open pore side is coated.

The polymers employed herein are available e. g. from Evonik and bear the designations L210s, L210, L09s, L207s, L206s (more slowly degradable PLGA-polymers) or RG502, RG502H, RG505 (more rapidly degradable PLGA-polymers), respectively.

In an application outside of the body, a matrix according to the description above may serve to fix cells which are exposed to an agent in a bioreactor. For example, in this manner defined cell types may be studied with regard to whether they respond to a medicament at issue or not, and the therapy can be planned in dependence of the observation results obtained thereby. Likewise, the development of medicaments may be simplified, because any toxicity is recognized at an early stage.

DESCRIPTION OF THE DRAWING

FIG. 1 describes the method of making the porous matrix for the implant.

The invention claimed is:

1. A matrix for cell implants having a connective porosity of more than 80%, comprising a mixture of bioresorbable polymers, wherein the matrix has a disk shape including two faces and a rim connecting the two faces, and wherein the surface on one face of the disk has a lesser average pore area proportion than the other face, wherein the matrix is made hydrophilic by a plasma deposition of a hydrophilic coating.

2. The matrix of claim 1, wherein the hydrophilic coating is poly(acrylic acid), PAA, wherein a partial PAA layer initially generated by the plasma deposition is thinner than a partial PAA layer subsequently generated without plasma deposition.

3. The matrix of claim 2, wherein the thickness of the coating is more than 1 µm.

4. The matrix of claim 1, wherein the matrix comprises poly((α-hydroxy) carboxylic acids).

5. The matrix of claim 1, wherein the matrix, outside an animal body, is infiltrated with viable cells and exposed to a test agent.

6. The matrix of claim 1, wherein the matrix is infiltrated with viable cells and subsequently placed within an animal body.

* * * * *